US009579483B2

(12) United States Patent
Belhe et al.

(10) Patent No.: US 9,579,483 B2
(45) Date of Patent: Feb. 28, 2017

(54) PRESSURE-SENSITIVE CONDUCTIVE COMPOSITE CONTACT SENSOR AND METHOD FOR CONTACT SENSING

(75) Inventors: Kedar Ravindra Belhe, Minnetonka, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1336 days.

(21) Appl. No.: 11/647,314

(22) Filed: Dec. 29, 2006

(65) Prior Publication Data
US 2008/0161786 A1 Jul. 3, 2008

(51) Int. Cl.
*A61B 5/00* (2006.01)
*A61M 25/00* (2006.01)
*A61B 18/14* (2006.01)

(52) U.S. Cl.
CPC .......... *A61M 25/00* (2013.01); *A61B 5/6885* (2013.01); *A61B 18/1492* (2013.01);
(Continued)

(58) Field of Classification Search
CPC .......... A61B 18/1492; A61B 2019/464; A61B 2019/465; H01C 10/106; H01C 7/027; G01L 1/20
(Continued)

(56) References Cited

U.S. PATENT DOCUMENTS 4,495,236 A * 1/1985 Obara et al. .................. 428/172
4,911,174 A 3/1990 Pederson
(Continued)

FOREIGN PATENT DOCUMENTS

| JP | 06-154154 | 6/1994 |
| JP | 09-135905 | 5/1997 |
| WO | 97/18754 | 5/1997 |

OTHER PUBLICATIONS

Peratech Ltd. (website page), QTC Pills, Retrofittable Components for Improved Switching Performance, Jan. 2004, www.peratech.co.uk.
(Continued)

*Primary Examiner* — Adam J Eiseman
(74) *Attorney, Agent, or Firm* — Wiley Rein LLP

(57) ABSTRACT

A catheter assembly for assessing contact between the catheter assembly and tissue is disclosed. The assembly includes a catheter shaft and a pressure sensitive conductive composite member whose electrical resistance varies with pressure applied to the catheter assembly. The assembly also includes at least one measurement terminal to permit the measurement of changes in the electrical characteristics of the pressure sensitive conductive composite member. The assembly may optionally include a measurement device to measure resistance, impedance and/or other electrical characteristics. The assembly may utilize a reference electrode secured to the patient's tissue, which permits the measurement device to measure changes between the reference electrode and the at least one measurement terminal. Optionally, the assembly may include a conductive outer layer. Also disclosed are sensor assemblies, contact sensor, methods of contact sensing, and methods of manufacturing relating to the use of pressure sensitive conductive composites.

7 Claims, 13 Drawing Sheets

(52) U.S. Cl.
CPC . *A61B 2090/064* (2016.02); *A61B 2562/0209* (2013.01); *A61M 2025/0002* (2013.01)

(58) Field of Classification Search
USPC .......... 600/374, 486, 488, 547, 561; 606/32; 128/899; 73/779
See application file for complete search history.

(56) References Cited

U.S. PATENT DOCUMENTS

| | | | |
|---|---|---|---|
| 5,028,394 A | | 7/1991 | Lowell, Jr. |
| 5,132,058 A | * | 7/1992 | Suyama ............. G01R 1/07342 264/104 |
| 5,313,840 A | * | 5/1994 | Chen et al. .................... 73/763 |
| 5,341,807 A | | 8/1994 | Nardella |
| 5,372,603 A | | 12/1994 | Acker |
| 5,382,247 A | | 1/1995 | Cimino et al. |
| 5,447,539 A | | 9/1995 | Kelly |
| 5,472,441 A | | 12/1995 | Edwards et al. |
| 5,545,161 A | | 8/1996 | Imran |
| 5,685,878 A | | 11/1997 | Falwell et al. |
| 5,697,925 A | | 12/1997 | Taylor |
| 5,836,990 A | | 11/1998 | Li |
| 5,868,737 A | | 2/1999 | Taylor |
| 5,913,854 A | | 6/1999 | Maguire et al. |
| 5,947,905 A | | 9/1999 | Hadjicostis |
| 6,013,074 A | | 1/2000 | Taylor |
| 6,039,731 A | | 3/2000 | Taylor |
| 6,066,139 A | | 5/2000 | Ryan |
| 6,113,592 A | | 9/2000 | Taylor |
| 6,113,593 A | | 9/2000 | Tu |
| 6,171,304 B1 | | 1/2001 | Netherly |
| 6,210,406 B1 | | 4/2001 | Webster |
| 6,217,573 B1 | | 4/2001 | Webster |
| 6,217,574 B1 | | 4/2001 | Webster |
| 6,221,023 B1 | | 4/2001 | Matsuba et al. |
| 6,246,898 B1 | | 6/2001 | Vesely |
| 6,264,653 B1 | | 7/2001 | Falwell |
| 6,272,371 B1 | | 8/2001 | Shlomo |
| 6,291,568 B1 | * | 9/2001 | Lussey ........................ 524/413 |
| 6,304,776 B1 | | 10/2001 | Muntermann |
| 6,322,558 B1 | | 11/2001 | Taylor |
| 6,325,799 B1 | | 12/2001 | Goble |
| 6,391,024 B1 | | 5/2002 | Sun |
| 6,423,057 B1 | | 7/2002 | He |
| 6,495,069 B1 | * | 12/2002 | Lussey et al. ................ 252/512 |
| 6,616,657 B2 | | 9/2003 | Simpson et al. |
| 6,620,159 B2 | | 9/2003 | Hedge |
| 6,638,222 B2 | | 10/2003 | Chandrasekaran et al. |
| 6,646,540 B1 | | 11/2003 | Lussey |
| 6,696,844 B2 | | 2/2004 | Wong |
| 6,730,082 B2 | | 5/2004 | Messing et al. |
| 6,845,264 B1 | | 1/2005 | Skladnev |
| 6,882,885 B2 | | 4/2005 | Levy, Jr. |
| 6,936,047 B2 | | 8/2005 | Nasab et al. |
| 6,974,457 B2 | | 12/2005 | Gibson |
| 6,999,821 B2 | | 2/2006 | Jenney et al. |
| 7,060,965 B2 | | 6/2006 | Vidovic |
| 7,205,983 B2 | * | 4/2007 | Raap et al. ................... 345/173 |
| 2002/0123749 A1 | | 9/2002 | Jain |
| 2004/0039298 A1 | | 2/2004 | Abreu |
| 2004/0133092 A1 | | 7/2004 | Kain |
| 2004/0133166 A1 | | 7/2004 | Moberg et al. |
| 2004/0215185 A1 | | 10/2004 | Truckai |
| 2005/0049583 A1 | | 3/2005 | Swanson |
| 2005/0119650 A1 | | 6/2005 | Sanders et al. |
| 2005/0137662 A1 | | 6/2005 | Morris et al. |
| 2005/0267332 A1 | | 12/2005 | Paul et al. |
| 2005/0267458 A1 | | 12/2005 | Paul et al. |
| 2006/0095022 A1 | | 5/2006 | Moll et al. |
| 2006/0111706 A1 | | 5/2006 | Truckai |
| 2006/0137464 A1 | | 6/2006 | Baudendistel |
| 2006/0147700 A1 | * | 7/2006 | Papakostas et al. .......... 428/323 |
| 2006/0249705 A1 | | 11/2006 | Wang et al. |
| 2006/0264831 A1 | | 11/2006 | Skwarek et al. |
| 2006/0278248 A1 | | 12/2006 | Viswanathan |

OTHER PUBLICATIONS

International Search Report of the International Searching Authority for PCT/US07/89099 dated Jul. 7, 2008.
International Search Report and Written Opinion of the International Searching Authority for PCT/US07/88723 dated Jul. 7, 2008.
International Search Report and Written Opinion of the International Searching Authority for PCT/US07/88680 dated Jul. 2, 2008.
Ghosh et al. Development of Layered Functional Fiber Based Micro-Tubes. National Textile Center Annual Report: Nov. 2005. Retrieved from the Internet on Jun. 24, 2008: <http://www.ntcresearch.org/pdf-rpts/AnRp05/F02-NS05-A5.pdf>.
NuSil R-2637 Product Profile Dec. 12, 2006.
International Search Report and Written Opinion of the International Searching Authority for PCT/US07/88729 dated May 16, 2008.
Mootanah, Rajshree et al., "Pressure Sensors", *Wiley Encyclopedia of Biomedical Engineering, Wiley Online Library: Book Abstract* Apr. 16, 2006.
Supplementary Partial European Search Report in EP Application No. 0786944.6 (Jun. 18, 2010).
Supplementary European Search Report in EP Application No. 07871747.7 (Jun. 24, 2011).
Title: Fiber Optic Interferometer Fabry-Perot Citation: http://physics.nad.ru/Physics/English/ifp_txt.htm Reference pp. 1-5 Publication Date: (actual publication date unknown).
Title: General Pharmacology Samba—Blood Pressure Systems Citation: http://www.bioseb.com/bioseb/anglais/default/item id=94 cat id=3 Samba%20-%20Pressure%20System.php Reference pp. 1-3 Publication Date: (actual publication date unknown).
Title: Micro Pressure Measurement System—Product Overview Citation: Biopac Systems, Inc. Reference pp. 1-39 Publication Date: Aug. 2007.
Title: Need to Know Citation: Medical Product Manuf. news Publication Date: Sep. 2007.
Title: Publications related to Samba Sensors Publication Date (actual publication date unknown).
Title: The Samba Technology Citation: Samba Sensors; www.samba.se/index2cfm?PageID=45 Publication Date: (actual publication date unknown).

* cited by examiner

PRESSURE-SENSITIVE CONDUCTIVE COMPOSITE CONTACT SENSOR AND METHOD FOR CONTACT SENSING

CROSS-REFERENCE TO RELATED APPLICATIONS

This application is related to U.S. application Ser. No. 11/647,316, filed Dec. 29, 2006, which is hereby incorporated by reference as though fully set forth herein.

BACKGROUND OF THE INVENTION a. Field of the Invention

The present invention pertains generally to an electrophysiological device and method for providing energy to biological tissue and, more particularly, to a contact sensor that is capable of being using with an ablation apparatus to provide greater contact sensitivity.

b. Background Art

Sensing devices, including tissue sensing devices, have heretofore been provided, but not pressure sensitive conductive composite ("PSCC") based sensors (including, for example, quantum tunneling composites ("QTC") and other pressure-sensitive, conductive polymers).

Many medical procedures, including for example, creating lesions with electrical energy, rely on good contact between the medical device and the tissue. In some catheter applications, the point of electrode-tissue contact is typically 150 cm away from the point of application of force. This gives rise to functional and theoretical challenges associated with conventional devices, and thus, the ability to accurately assess tissue contact is increasingly important.

There is a need for contact sensing devices that provide greater contact sensitivity for control of medical treatments.

There is a need for improved sensor devices that provide greater contact sensitivity, especially in connection with RF ablation treatments.

BRIEF SUMMARY OF THE INVENTION

Disclosed in one embodiment is a catheter assembly for assessing contact between the catheter assembly and tissue, which assembly includes a catheter shaft and a pressure sensitive conductive composite member whose electrical resistance varies with pressure applied to the catheter assembly. The assembly also includes at least one measurement terminal to permit the measurement of changes in resistance of the pressure sensitive conductive composite member. The assembly may optionally include a measurement device coupled to the at least one measurement terminal to measure changes in resistance of the pressure sensitive conductive composite member. The assembly may utilize a reference electrode secured to the patient's tissue, which will permit the measurement device to measure changes in the resistance of the pressure sensitive conductive composite member based on changes in electrical characteristics between the reference electrode and the at least one measurement terminal. In some instances, the reference electrode may be connected to an electrical ground. The pressure sensitive conductive composite member may be made of a quantum tunneling composite or another pressure sensitive conductive composite medium.

Also disclosed is a sensor assembly for assessing contact between the sensor assembly and tissue, wherein the assembly includes a catheter shaft, a catheter tip; and a quantum tunneling composite member having a first end and a second end, and being located between the catheter shaft and the catheter tip. A measurement device may be coupled to each of the first end and the second end of the quantum tunneling composite member such that said measurement device measures an electrical characteristic of the quantum tunneling composite member. The catheter assembly is preferably assembled such that a pressure applied to the catheter tip is transferred to the quantum tunneling composite member and the pressure changes the electrical characteristic of said quantum tunneling composite member. The measurement device then measures the change in electrical characteristics of the quantum tunneling composite member.

Disclosed herein is also another sensor assembly for assessing contact between the sensor assembly and tissue, the assembly having a catheter shaft, a conductive core having a first measurement terminal, and a layer of a pressure sensitive conductive composite in electrical contact with said conductive core. Preferably, the pressure sensitive conductive composite layer includes a tissue contact surface that may be placed in contact with tissue. The assembly may also include a measurement device coupled to the first measurement terminal such that the measurement device measures an electrical characteristic of the pressure sensitive conductive composite such than the measurement provides a user with useful information regarding the degree of contact between the sensor assembly and the tissue being contacted. Optionally, a memory and a process are coupled to the measurement device. The memory stores a plurality of electrical characteristic measurements, and the processor assesses the degree of contact using a plurality of measurements stored in the memory. The assembly may include a reference electrode with a second reference terminal for securing to the patient's tissue, which permits the measurement device to measure the electrical characteristics of the pressure sensitive conductive composite using the first and second terminals. Optionally, the assembly includes a conductive outer layer having a second measurement terminal wherein the conductive outer layer covers at least a portion of the layer of pressure sensitive conductive composite. The measurement device can then measure the electrical characteristics of the layer of pressure sensitive conductive composite using the first measurement terminal and the second measurement terminal. Optionally, the assembly includes a non-conductive outer layer (which may be rigid or flexible) covering at least a portion of the conductive outer layer.

Also disclosed herein is a method of sensing contact between a catheter and tissue, which includes: providing a catheter having a catheter shaft and at least one quantum tunneling composite material; placing the catheter in contact with a patient's tissue such that pressure is asserted on the quantum tunneling composite material; and sensing a signal that is indicative of the degree of contact that exists between the catheter and the tissue. The signal being sense may be resistance that is measured along a path of the quantum tunneling composite material. For example, the signal may indicate that the measured resistance having dropped below a set threshold, thereby indicating a desired level of contact between the catheter and the tissue. Other techniques may be used to sense the signal, including, for example, applying a reference electrode to tissue that will be placed in contact with the catheter and measuring the impedance of a path including at least the reference electrode and at least a portion the quantum tunneling composite material. Alternatively, the technique may include setting a pressure threshold that is representative of a desired level of contact between the quantum tunneling composite material and the tissue;

measuring the impedance along a path of the quantum tunneling composite material; and then generating a signal that is a degree of contact between the quantum tunneling composite material and the tissue has exceeded the pressure threshold.

Also disclosed is a contact sensor assembly for assessing contact between the contact sensor assembly and tissue. The assembly includes an elongate catheter body having a proximal end and a distal end, a conductive core (having a first measurement terminal) extending at least a portion of the distal end, a pressure sensitive conductive composite member electrically coupled to at least a portion of the conductive core located in the distal end of the catheter body. A conductive layer having a second measurement terminal covers at least a portion of the pressure sensitive conductive composite member, and the conductive layer extends at least a portion of the distal end of the catheter body. The electrical characteristics of the pressure sensitive conductive composite member may be measured using the first measurement terminal and the second measurement terminal. A measurement device may be used to measure a signal using the first and second measurement terminals and to generate an output signal that is indicative of the pressure being applied to the tissue by the distal end.

Also disclosed is a method of sensing contact between a catheter and tissue. The method involves placing a catheter having a catheter shaft and a pressure sensitive conductive composite element, in contact with a tissue. The electrical characteristics of the pressure sensitive conductive composite element may be monitored for a change that is indicative of contact having been made between the catheter and tissue. The catheter may include an electrode tip of a material that is not the same as the material comprising the pressure sensitive conductive composite element, where the electrode tip is in contact with the pressure sensitive conductive composite element. In this configuration, the electrode tip is placed in contact with the tissue such that pressure is exerted on the pressure sensitive conductive composite element. Measuring the electrical characteristics may involve measuring the impedance along a path of the pressure sensitive conductive composite element and then using the measured impedance to generating a signal that is indicative of pressure that exists between the electrode tip and the tissue. The impedance may be correlated to pressure levels. For example, a known pressure may be applied to the catheter and then the electrical characteristic recorded for the known pressure level. Additional known pressures may be applied, with their corresponding measurements recorded. An analysis program may use this information to assess the value of an unknown pressure in light of the plurality of recorded characteristics.

Finally, a method of manufacturing a contact sensor is disclosed. A catheter shaft having a distal end and a proximal end is formed. A conductive core formed extending from the distal end of the catheter shaft, where the conductive core has a first measurement terminal that is electrically coupled to the conductive core. A distal end of the contact sensor is then formed using pressure sensitive conductive composite material covering at least a portion of the conductive core. The first measurement terminal may be connected to an analyzer for analyzing the electrical characteristics of the pressure sensitive conductive composite material. The distal end may be formed by coating the conductive core with a layer of a quantum tunneling composite material. The conductive core may be formed of materials all of which are conductive, or alternatively, an electrically conductive element may be formed over a electrically non-conductive shaft (which may be flexible or rigid). The conductive element may be formed as a helical coil, or a wire mesh. An outer conductive layer may be formed over at least a portion of the pressure sensitive conductive composite material; and an analyzer may then be used to analyze the electrical characteristics of the pressure sensitive conductive composite material using the outer conductive layer as one terminal and the inner conductive core as a second terminal.

An object of the present invention is to provide a contact sensor assembly that can assess contact with tissue based on the degree of pressure that is exerted on the sensor.

Another object of the present invention is to provide a flexible contact sensor that measures pressure that is being exerted on the sensor based on direct or indirect contact between the sensor and another mass, such as tissue.

Yet another object of the present invention is to provide a method of contact sensing.

Yet another object of the present invention is to provide a method of manufacturing a contact sensor.

An objective of the present invention is to provide a pressure-sensitive, conductive composite-based sensor that may be used in connection with RF ablation treatment.

An objective of the present invention is to provide a QTC-based sensor that may be used in connection with RF ablation treatment.

Another object of the present invention is to provide a flexible, contact-sensitive sensor that can be used in a wide variety of tissue environments.

Yet another objective of this invention is to provide a method for practicing medical procedures using a pressure-sensitive, conductive polymer-based sensor in accordance with the teachings herein.

An advantage of using a PSCC in a contact sensor is that the design may be significantly less complicated, which permits reduced manufacturing costs and increased reliability.

The foregoing and other aspects, features, details, utilities, and advantages of the present invention will be apparent from reading the following description and claims, and from reviewing the accompanying drawings.

DETAILED DESCRIPTION OF THE INVENTION

Figure 1A:
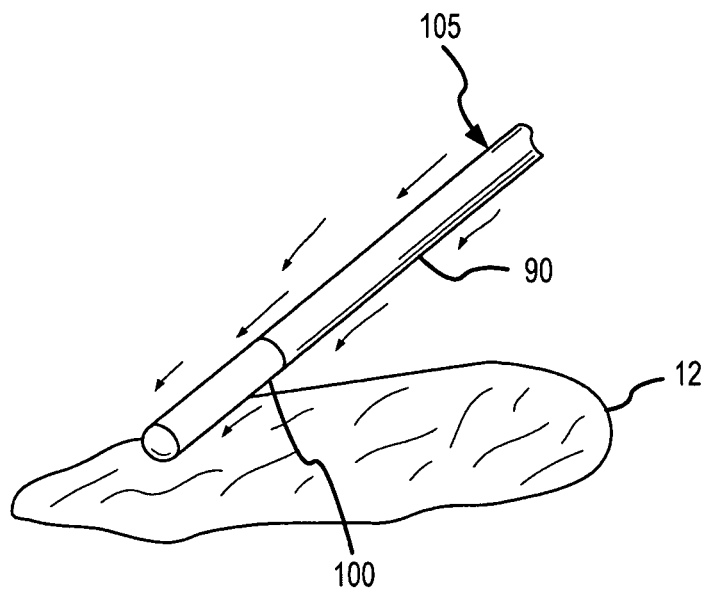
FIGS. 1A and 1B are perspective views of a sample embodiment of the present invention, illustrating how the present invention may be used to assess contact with tissue.

A flexible PSCC-based contact sensor is disclosed, together with a method of using and a method of manufacturing.

When used in this application, the terms "pressure sensitive conductive composite" and "PSCC" mean a pressure sensitive conductive composite that has unique electrical properties as follows: the electrical resistance of the PSCC varies inversely in proportion to the pressure that is applied to the PSCC. The PSCC material that is most useful with the present invention has a high electrical resistance when not under stress (that is, in a quiescent state), and yet the same PSCC material starts to become conductive under pressure, and indeed, the electrical resistance may fall to less than one ohm (1Ω) when under sufficient pressure. When in a quiescent state, the PSCC material preferably has a resistance that is greater than 100,000 ohms, and more preferably, greater 1 M ohms, and most preferably, the PSCC material is a non-conductor in its quiescent state (e.g., having a resistance greater than 10 M ohms). Preferably, the PSCC material will also meet cytotoxity, hemolysis, systemic toxicity and intracutaneous injection standards.

The present invention will work with different materials. For example, U.S. Pat. No. 6,999,821 (which is incorporated by reference herein as if fully set forth below) discloses a conductor-filled polymer that may be useful in the present invention. As disclosed therein, conductor-filled polymers may include presently available materials approved for implantation in a human body such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637. The substrate need not be silicone; for example, it is contemplated that other insulating or weakly conductive materials (e.g., non-conductive elastomers) may be embedded with conductive materials, conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series and if appropriate, at least one electroconductive agent). The conductive material may be in the form of powder, grains, fibers or other shaped forms. The oxides can be mixtures comprising sintered powders of an oxycompound. The alloy may be conventional or for example titanium boride.

Other examples of an acceptable PSCCs for use in the present invention include quantum tunneling composites ("QTC"), such as those available through Peratech Ltd. (of Darlington, UK), including the QTC pill, the QTC substrate and the QTC cables. The QTC materials designed by Peratech Ltd. have variable resistance values that range from >10 M ohms (in the absence of stress) to <1 ohm when under pressure. Ideally, the QTC would meet cytotoxity, hemolysis, systemic toxicity and intracutaneous injection standards.

Other examples of PSCC materials that may be used in the present invention include the conductive polymers described and disclosed in U.S. Pat. No. 6,646,540 ("Conductive Structures"); U.S. Pat. No. 6,495,069 ("Polymer Composition"); and U.S. Pat. No. 6,291,568 ("Polymer Composition"); all of the foregoing patents are incorporated by reference as if set forth below in their entireties. These materials as described has having a variable resistance of >$10^{12}$ Ohms before any stress is applied to less than 1 ohm when finger pressure is applied.

As a result of this unique property, PSCC materials may be described as having an ability to transform from an effective insulator to a metal-like conductor when deformed by compression, twisting, or stretching. The electrical response of a PSCC can be tuned appropriately to the spectrum of pressures being applied. Its resistance range often varies from greater than 10 MΩ to less than 1Ω. The transition from insulator to conductor often follows a smooth and repeatable curve, with the resistance dropping monotonically to the pressure applied. Moreover, the effect is reversible in the sense that once the pressure is removed, the electrical resistance is also restored. Thus, a PSCC may be transformed from an insulator to a conductor, and back to an insulator, simply by applying the appropriate pressure. PSCCs have been known to carry large currents (up to 10 Amps) and support large voltages (40 V and higher).

Preferably, the PSCC being used in connection with the present invention can transform from an insulator (that is, conducting little or no current) to an effective conductor simply by applying a small change in pressure to the PSCC. For example, by applying pressure with a hand, or more particularly, with a finger, a surgeon can transform the PSCC from an insulator to a conductor to permit contact sensing.

The PSCC used in the present invention may also be chosen or customized to be of a specific pressure sensitivity such that the transformation from an insulator to a conductor occurs over a wide or narrow range of pressure. For example, highly sensitive PSCCs, which register a sharp change in resistance with a finite amount of applied pressure, may be preferred for soft contact applications such as the atrial wall. Less sensitive PSCCs, which require more pressure to register the same amount of change in resistance, may be preferred for hard contact applications such as ablation in ventricular walls.

The unique properties of a PSCC permit the creation of novel and pressure-sensitive current-control devices for the evaluating tissue contact. The unique properties also permit the creation of novel and pressure-sensitive sensors to assess contact between the sensors and tissue that may be the subject of ablation.

Figure 1B:
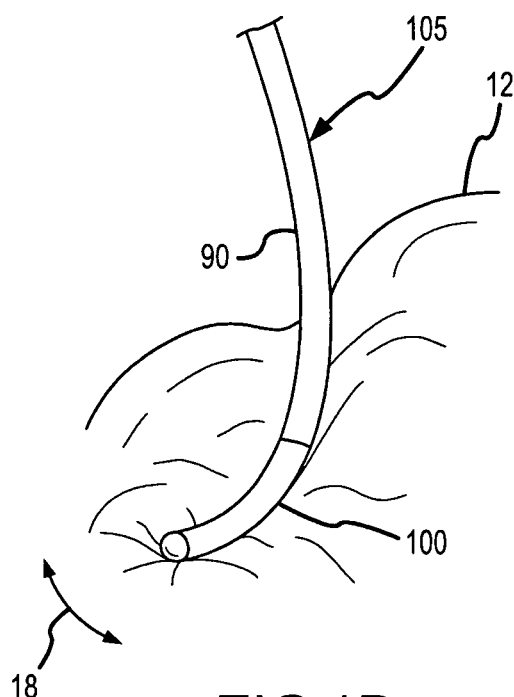

FIGS. 1A and 1B illustrate a sample embodiment of the present invention. As illustrated in FIGS. 1A and 1B, PSCC contact sensor 105 includes a catheter shaft 90 and a contact surface 100 that extends from catheter shaft 90. In this embodiment, contact sensor 105 is flexible such that when it comes into contact with tissue 12, contact sensor 105 is deflected in direction 18 as illustrated in FIG. 1b, and the deflection permits the degree of contact between contact sensor 105 and tissue 12 to be assessed.

Figure 2:
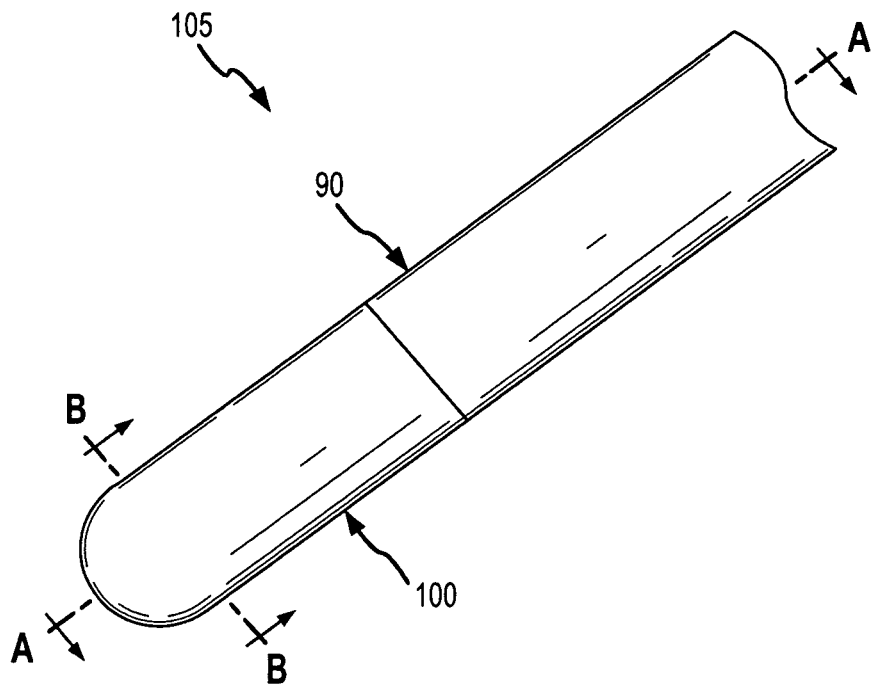
FIG. 2 is a side view drawing of an exemplary catheter having a PSCC sensor.

FIG. 2 is a close-up of the sample embodiment depicted in FIGS. 1A and 1B. FIG. 2 illustrates cross-sectional reference lines A-A and B-B, which will be used to illustrate preferred embodiment of the present invention.

Figure 3A:
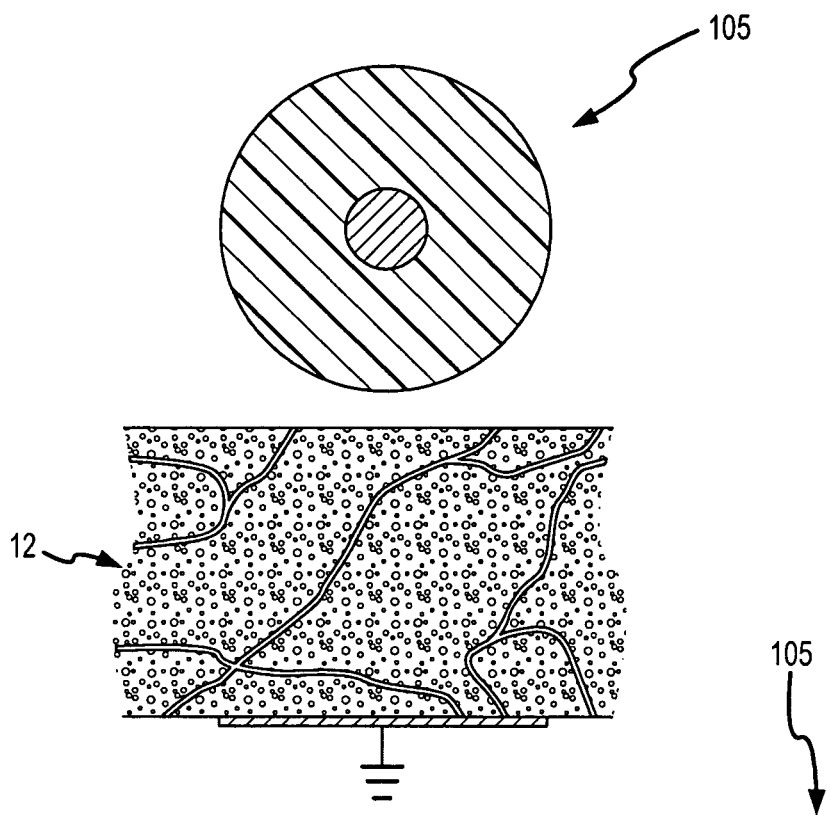
FIGS. 3A and 3B are cross sectional views that demonstrate the contact pressure at the sensor-tissue interface.
Figure 3B:
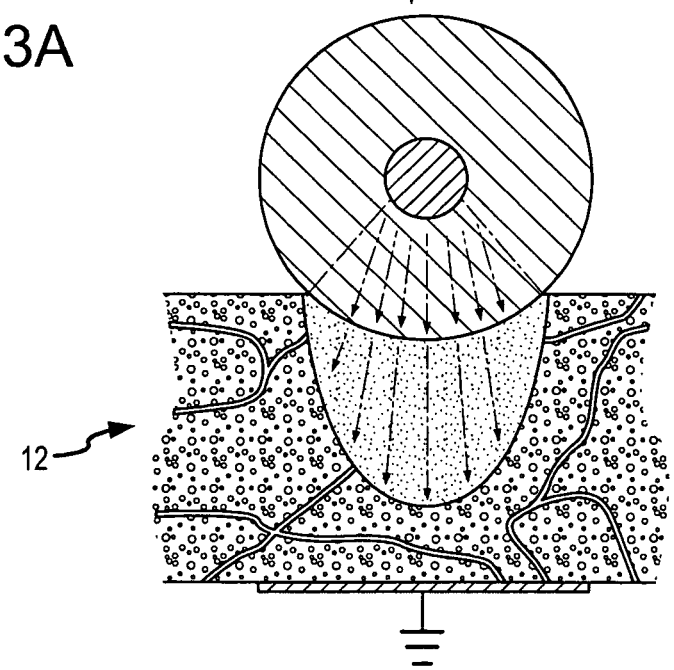

As illustrated in FIG. 3A, when the PSCC sensor is in a relatively contact free environment (such as air, or in the flowing blood stream while inside a blood vessel or heart chamber), the PSCC is an insulator. When used for a sensing application, however, the PSCC sensor is placed against tissue as illustrated in FIG. 3B. As the contact pressure increases, the PSCC becomes conductive and permits the degree of contact to be assessed by the sensing device. Because of the unique properties of a PSCC, only that portion of the PSCC sensor that is in contact with the tissue becomes conductive. Those portions which are not in direct contact with the tissue, such as the region facing the blood, remain non-conductive, thereby mitigating any current leakage that may cause coagulum and thrombus formation.

The resistance of a PSCC sensor changes anisotropically, based on the variation of the contact pressure on the PSCC sensor. Thus, as illustrated in FIG. 3B, the contact pressure at the sensor-tissue interface is maximum at the point (or line) of normal incidence and gradually decreases along the arc of contact to zero at the edge of the contact. Because of its ability to detect stress forces in any direction, the sensor can be designed to be omni-directional in use.

Figure 4A:
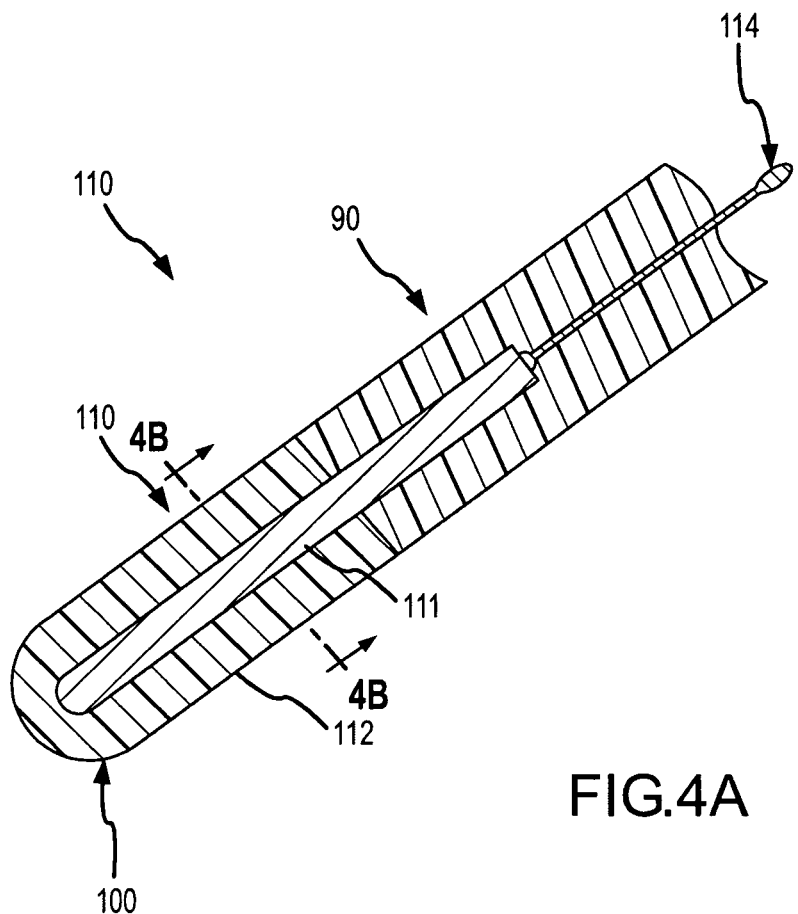
FIGS. 4A and 4B are cross-sectional views of a preferred embodiment of a catheter having a PSCC sensor.
Figure 4B:
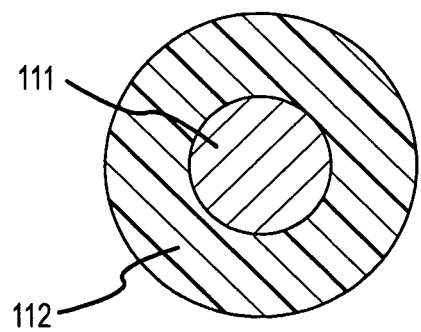

FIGS. 4A and 4B illustrate a preferred embodiment of the present invention, revealing two cross sectional drawings taken along the reference lines of A-A and B-B as labeled in FIG. 2.

In FIGS. 4A and 4B, PSCC contact sensor 110 includes a catheter shaft 90 and a contact surface 100 that extends from catheter shaft 90. Catheter shaft 90 may be either conductive or non-conductive, and preferably, catheter shaft 90 is non-conductive. In this embodiment, the PSCC forms the working surface of the sensor that is used for contact assessment. As depicted in FIGS. 4A and 4B, PSCC sensor 110 comprises: flexible inner conductive core 111; and an outer PSCC substrate layer 112, which is mechanically and electrically coupled to the flexible inner conductive core 111. Flexible inner conductive core 111 may include a flat top (like the top of a right cylinder), or optionally it may include a portion of a sphere on its distal end as illustrated in FIG. 4A. Flexible inner conductive core 111 may be connected to an electrical conductor 114, which may be connected to an analyzer (not shown). In use, this preferred embodiment is used to assess contact between PSCC sensor 110 and tissue (not shown) to which a reference electrode (not shown) has been attached. PSCC sensor 110 assesses the contact between contact surface 100 and the subject tissue by monitoring the electrical characteristics between two nodes, namely, the reference electrode (not shown) and the flexible inner conductive core 111 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 110. Preferably, the reference electrode is grounded to an electrical ground reference signal.

Figure 5A:
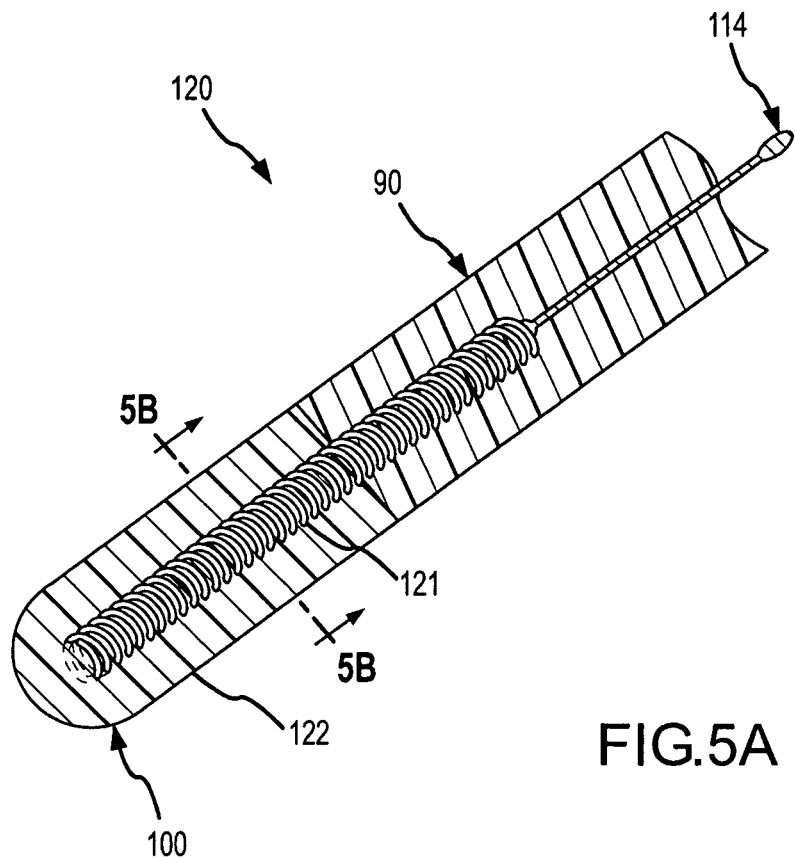
FIGS. 5A and 5B are cross-sectional views of a preferred embodiment in which the PSCC sensor is in the shape of a helix.
Figure 5B:
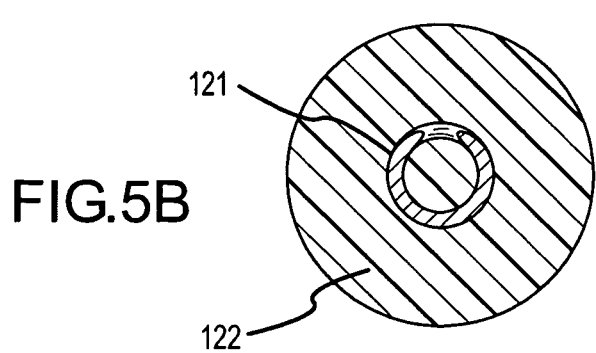

FIGS. 5A and 5B illustrate another preferred embodiment of the present invention, revealing two cross sectional drawings taken along the reference lines of A-A and B-B as labeled in FIG. 2. PSCC sensor 120 extends from a catheter shaft 90, and PSCC sensor 120 comprises: flexible inner conductive coil 121 in the shape of a helix; and a PSCC substrate layer 122 within which the inner conductive coil 121 is located. Flexible inner conductive coil 121 is connected to an electrical conductor 114, which may be connected to an analyzer (not shown). In use, this preferred embodiment is used to assess contact between PSCC sensor 120 and tissue (not shown) to which a reference electrode (not shown) has been attached. PSCC sensor 120 assesses the contact between contact surface 100 and the subject tissue by monitoring the electrical characteristics between two nodes, namely, the reference electrode (not shown) and the flexible inner conductive coil 121 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 120. Preferably, the reference electrode is grounded to an electrical ground reference signal.

Figure 6A:
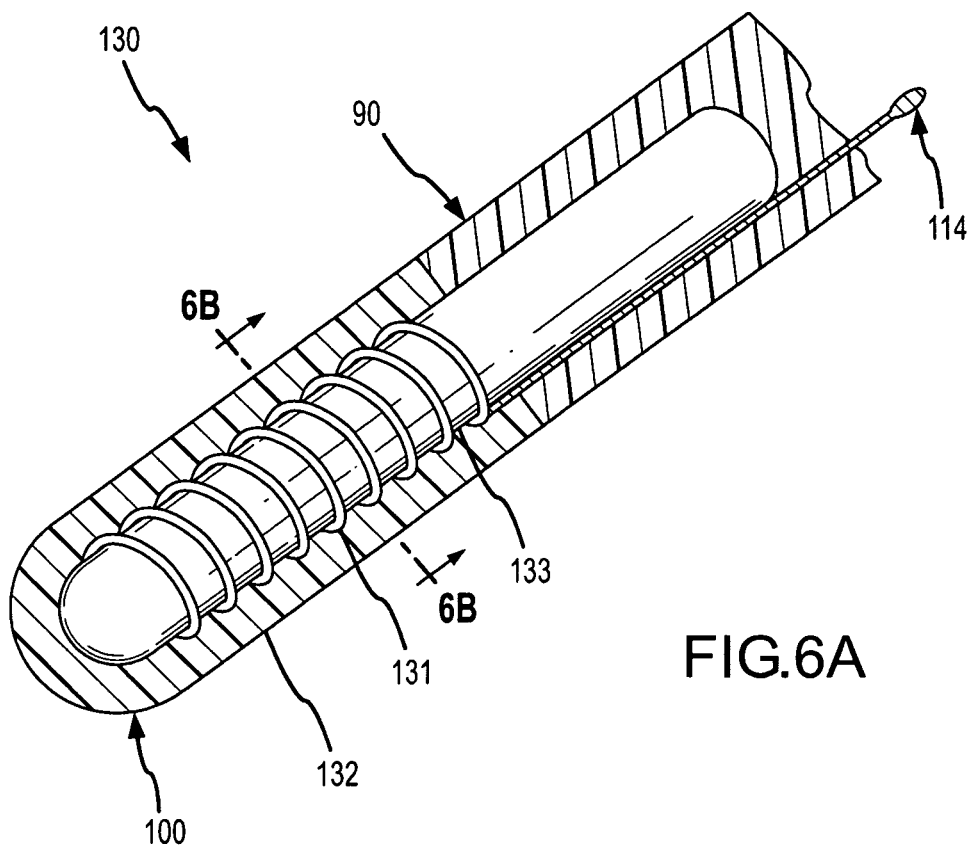
FIGS. 6A and 6B are cross-sectional views of another preferred embodiment in which the PSCC sensor is located about an inner conductive core.
Figure 6B:
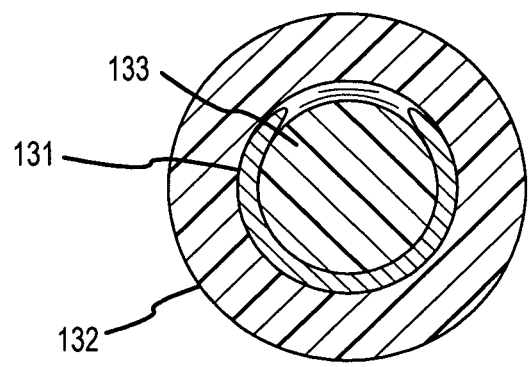

FIGS. 6A and 6B illustrate yet another preferred embodiment of the present invention, revealing two cross sectional drawings taken along the reference lines of A-A and B-B as labeled in FIG. 2. PSCC sensor 130 extends from a catheter shaft 90, and PSCC sensor 130 comprises: flexible inner conductive coil 131 in the shape of a helix; an outer PSCC substrate layer 132; and an electrically insulative flexible shaft 133 located within the helix of the flexible inner conductive coil 131. Flexible shaft 133 may optionally include a portion of a sphere on its distal end as shown in FIG. 6A. Flexible inner conductive coil 131 is connected to an electrical conductor 114, which may be connected to an analyzer (not shown). In use, this preferred embodiment is used to assess contact between PSCC sensor 130 and tissue (not shown) to which a reference electrode (not shown) has been attached. PSCC sensor 130 assesses the contact between contact surface 100 and the subject tissue by monitoring the electrical characteristics between two nodes, namely, the reference electrode (not shown) and the flexible inner conductive coil 131 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 130. Preferably, the reference electrode is grounded to an electrical ground reference signal.

Figure 7A:
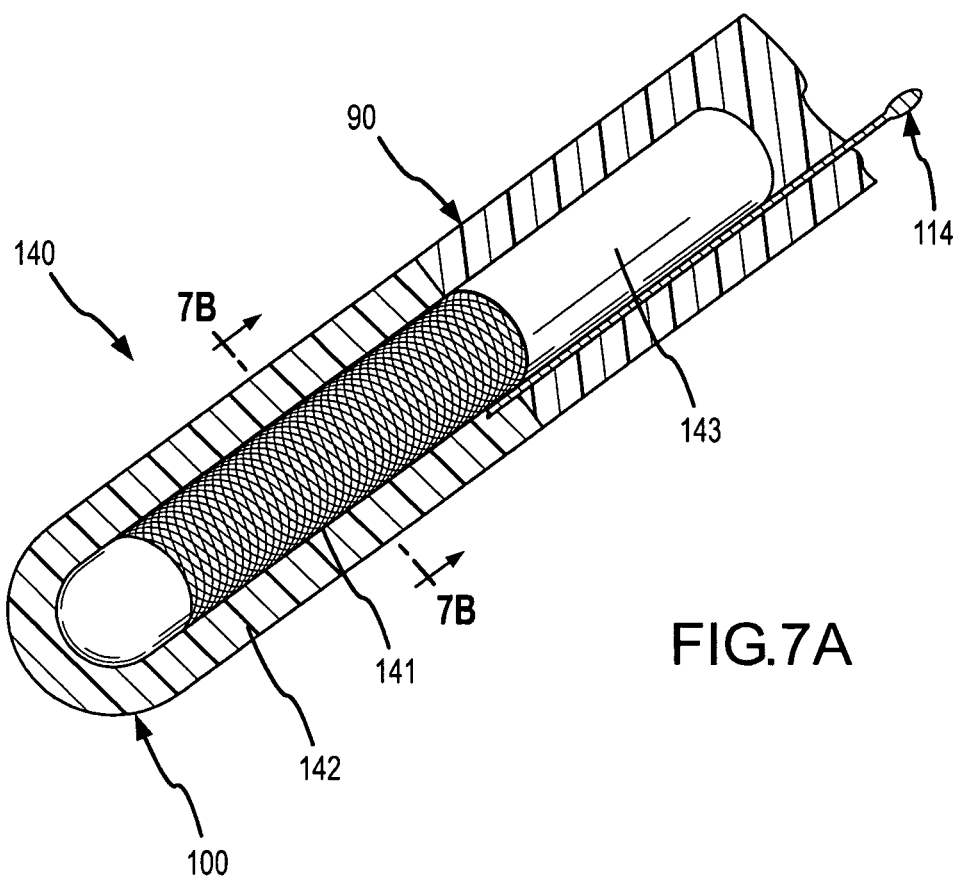
FIGS. 7A and 7B are cross-sectional views of another preferred embodiment in which the PSCC sensor is in the shape of a mesh.
Figure 7B:
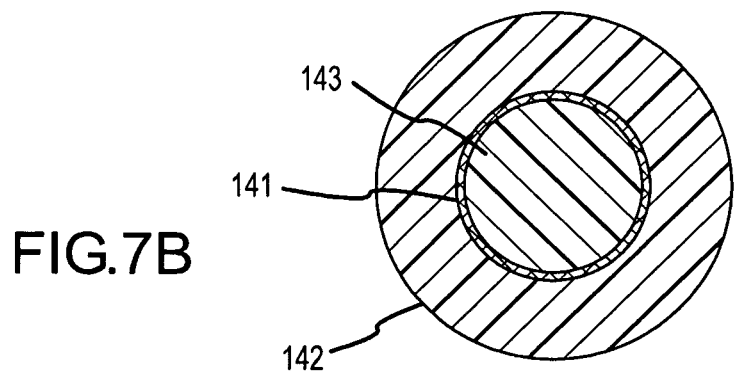

FIGS. 7A and 7B illustrate yet another preferred embodiment of the present invention, revealing two cross sectional drawings taken along the reference lines of A-A and B-B as labeled in FIG. 2. PSCC sensor 140 extends from a catheter shaft 90, and PSCC sensor 140 comprises: flexible inner conductive sheath 141 formed of a mesh; an outer PSCC substrate layer 142; and an electrically insulative flexible shaft 143 located interiorly of the flexible inner conductive sheath 141. Flexible shaft 143 may optionally include a portion of a sphere at its distal end as shown in FIG. 7A. Flexible sheath 141 is connected to an electrical conductor 114, which may be connected to an analyzer (not shown). In use, this preferred embodiment is used to assess contact between PSCC sensor 140 and tissue (not shown) to which a reference electrode (not shown) has been attached. PSCC sensor 140 assesses the contact between contact surface 100 and the subject tissue by monitoring the electrical characteristics between two nodes, namely, the reference electrode (not shown) and the flexible sheath 141 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 140. Preferably, the reference electrode is grounded to an electrical ground reference signal.

Figure 8A:
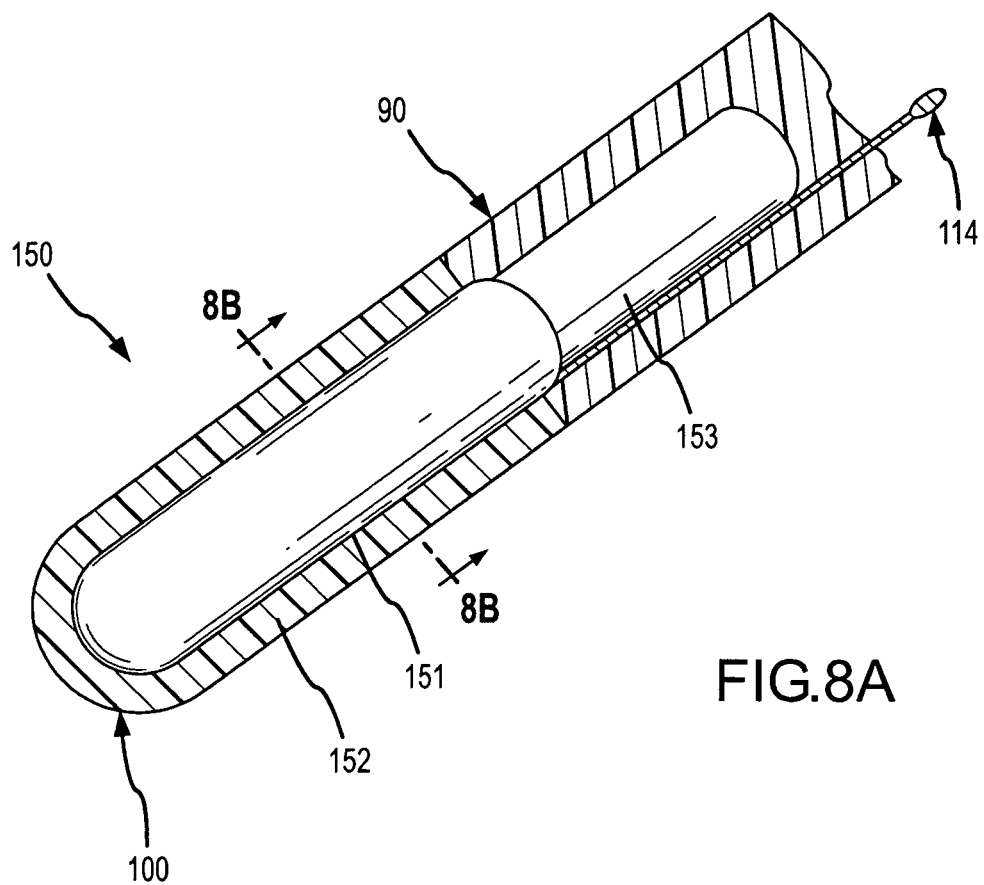
FIGS. 8A and 8B are cross-sectional views of another preferred embodiment in which the PSCC sensor is formed as an outer substrate layer.
Figure 8B:
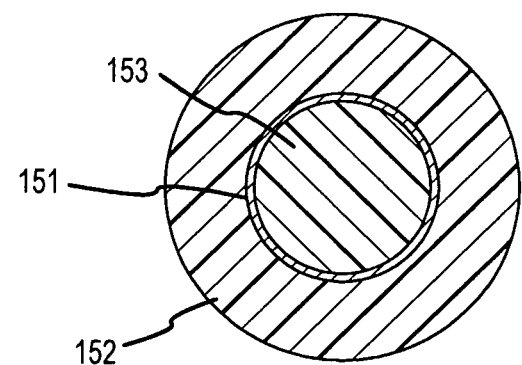

FIGS. 8A and 8B illustrates yet another preferred embodiment of the present invention, revealing two cross sectional drawings taken along the reference lines of A-A and B-B as labeled in FIG. 2. PSCC sensor 150 extends from a catheter shaft 90, and PSCC sensor 150 comprises: an electrically insulative flexible shaft 153; a flexible inner conductive layer 151 (formed, for example, as a coating and/or wrap around flexible shaft 153); and an outer PSCC substrate layer 152. Electrically insulative flexible shaft 153 and flexible inner conductive layer 151 may optionally include a portion of a sphere at their respective distal ends (as illustrated in FIG. 8A). Flexible inner conductive core 151 is connected to an electrical conductor 114, which may be connected to an analyzer (not shown). In use, this preferred embodiment is used to assess contact between PSCC sensor 150 and tissue (not shown) to which a reference electrode (not shown) has been attached. PSCC sensor 150 assesses the contact between contact surface 100 and the subject tissue by monitoring the electrical characteristics between two nodes, namely, the reference electrode (not shown) and the flexible inner conductive core 151 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 150. Preferably, the reference electrode is grounded to an electrical ground reference signal.

Figure 9A:
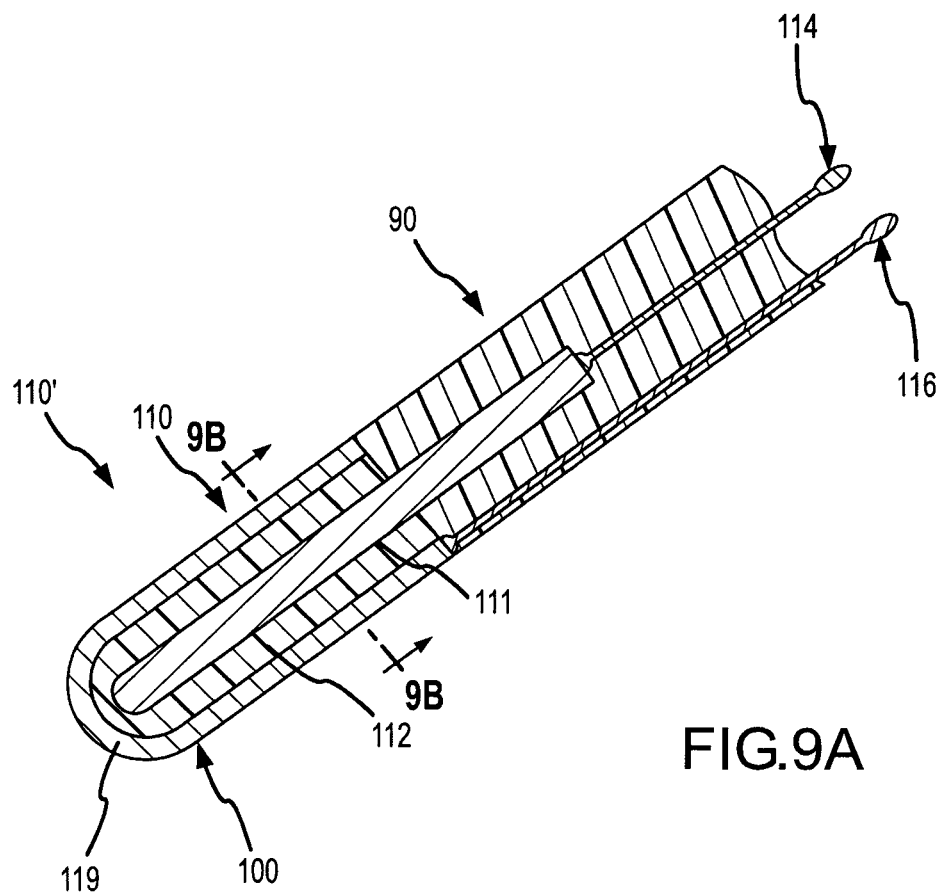
FIGS. 9A and 9B are cross-sectional views of a preferred embodiment of a catheter having a PSCC sensor.
Figure 9B:
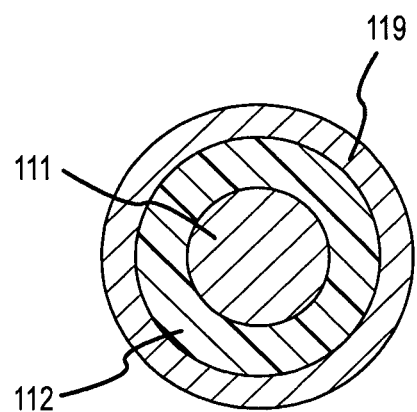

FIGS. 9A and 9B illustrate a preferred embodiment of the present invention, revealing two cross sectional drawings taken along the reference lines of A-A and B-B as labeled in FIG. 2. FIG. 9A is a variation of the preferred embodiment illustrated in FIG. 4A. In FIGS. 9A and 9B, PSCC contact sensor 110' includes a catheter shaft 90 and a contact surface 100 that extends from catheter shaft 90. Catheter shaft 90 may be either conductive or non-conductive, and preferably, catheter shaft 90 is non-conductive. As depicted in FIG. 9A, PSCC sensor 110' comprises: flexible inner conductive core 111; and an outer PSCC substrate layer 112, which is mechanically and electrically coupled to the flexible inner conductive core 111. Flexible inner conductive core 111 may optionally include a portion of a sphere on its distal end, as illustrated in FIG. 9A. Flexible inner conductive core 111 may be connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 110' and tissue by monitoring the electrical characteristics between two nodes, namely, the conductive outer layer 119 (which is preferably measured using electrical conductor 116) and the flexible inner conductive core 111 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 10A:
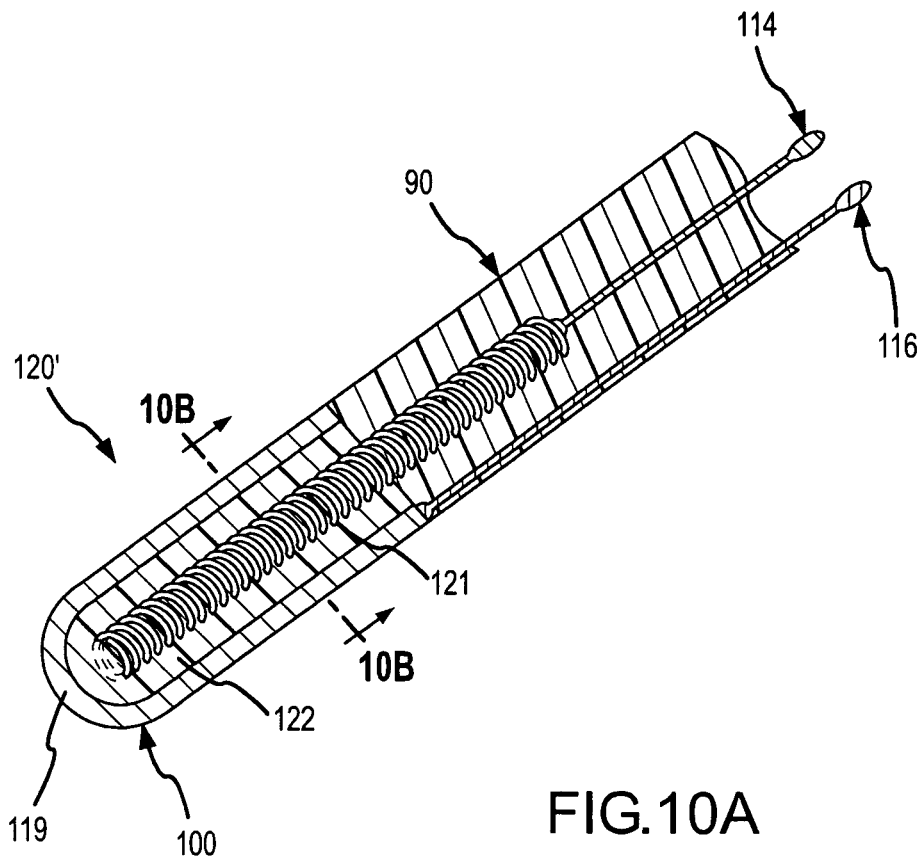
FIGS. 10A and 10B are cross-sectional views of another preferred embodiment in which the PSCC sensor is in the shape of a helix.
Figure 10B:
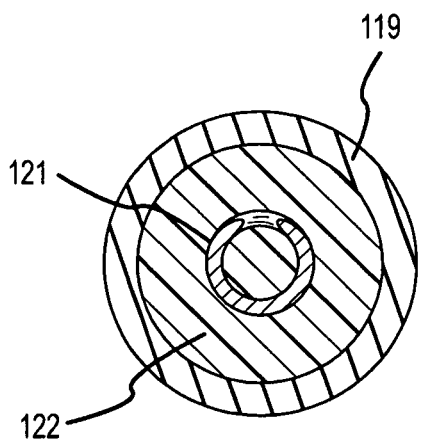

FIGS. 10A and 10B illustrate another preferred embodiment of the present invention, revealing two cross sectional drawings taken along the reference lines of A-A and B-B as labeled in FIG. 2. FIG. 10A is a variation of the preferred embodiment illustrated in FIG. 5A. PSCC sensor 120' extends from a catheter shaft 90, and PSCC sensor 120' comprises: flexible inner conductive coil 121 in the shape of a helix; and a PSCC substrate layer 122 within which the inner conductive coil 121 is located. Flexible inner conductive coil 121 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 120' and tissue by monitoring the electrical characteristics between two nodes, namely, the conductive outer layer 119 (which is preferably measured using electrical conductor 116) and the flexible inner conductive coil 121 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 11A:
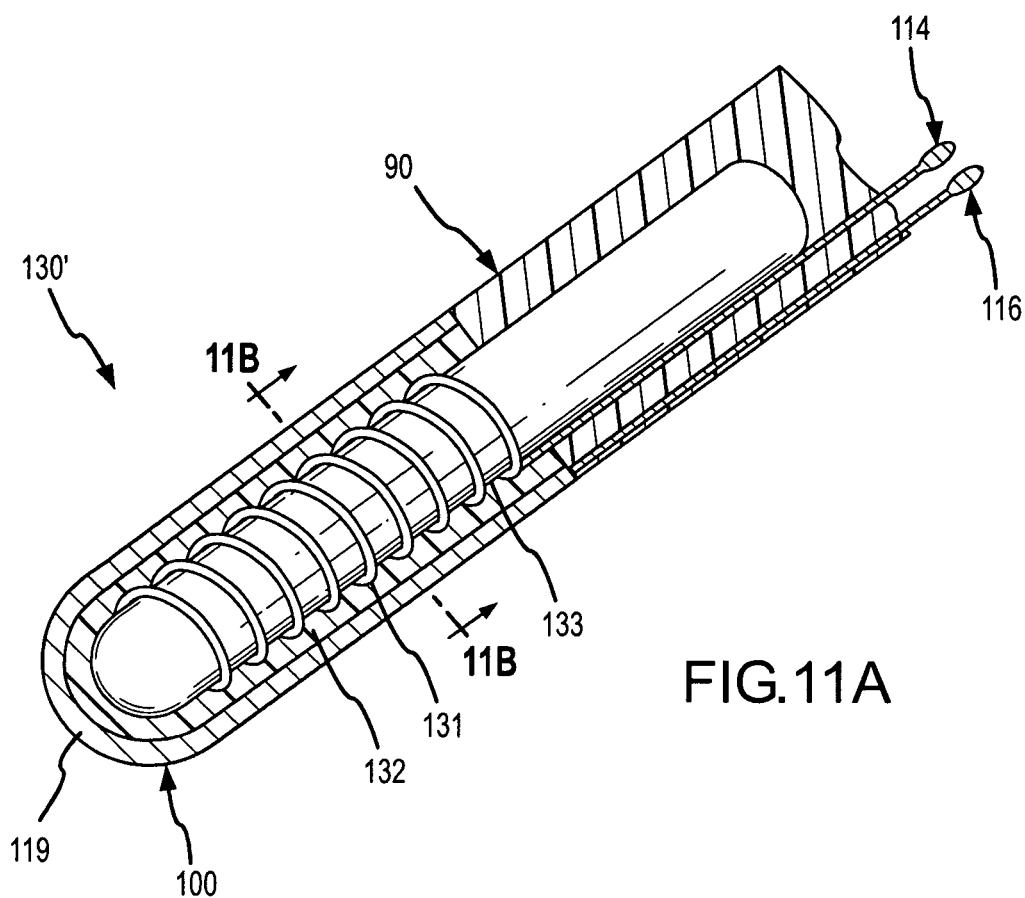
FIGS. 11A and 11B are cross-sectional views of another preferred embodiment in which the PSCC sensor is located about an inner conductive core.
Figure 11B:
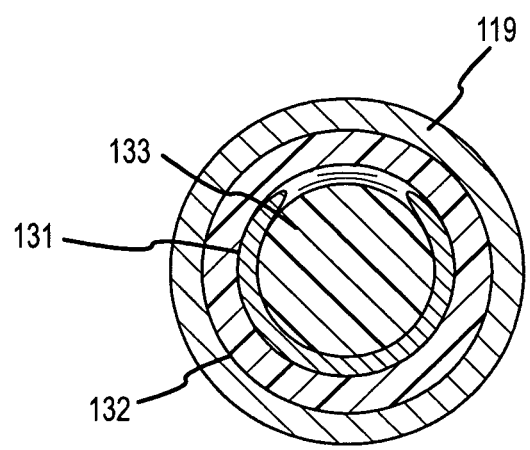

FIGS. 11A and 11B illustrate yet another preferred embodiment of the present invention, revealing two cross sectional drawings taken along the reference lines of A-A and B-B as labeled in FIG. 2. FIG. 11A is a variation of the preferred embodiment illustrated in FIG. 6A. PSCC sensor 130' extends from a catheter shaft 90, and PSCC sensor 130' comprises: flexible inner conductive coil 131 in the shape of a helix; an outer PSCC substrate layer 132; and an electrically insulative flexible shaft 133 located within the helix of the flexible inner conductive coil 131. Flexible shaft 133 may optionally include a portion of a sphere on its distal end as shown in FIG. 11A Flexible inner conductive coil 131 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 130' and tissue by monitoring the electrical characteristics between two nodes, namely, the conductive outer layer 119 (which is preferably measured using electrical conductor 116) and the flexible inner conductive coil 131 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 12A:
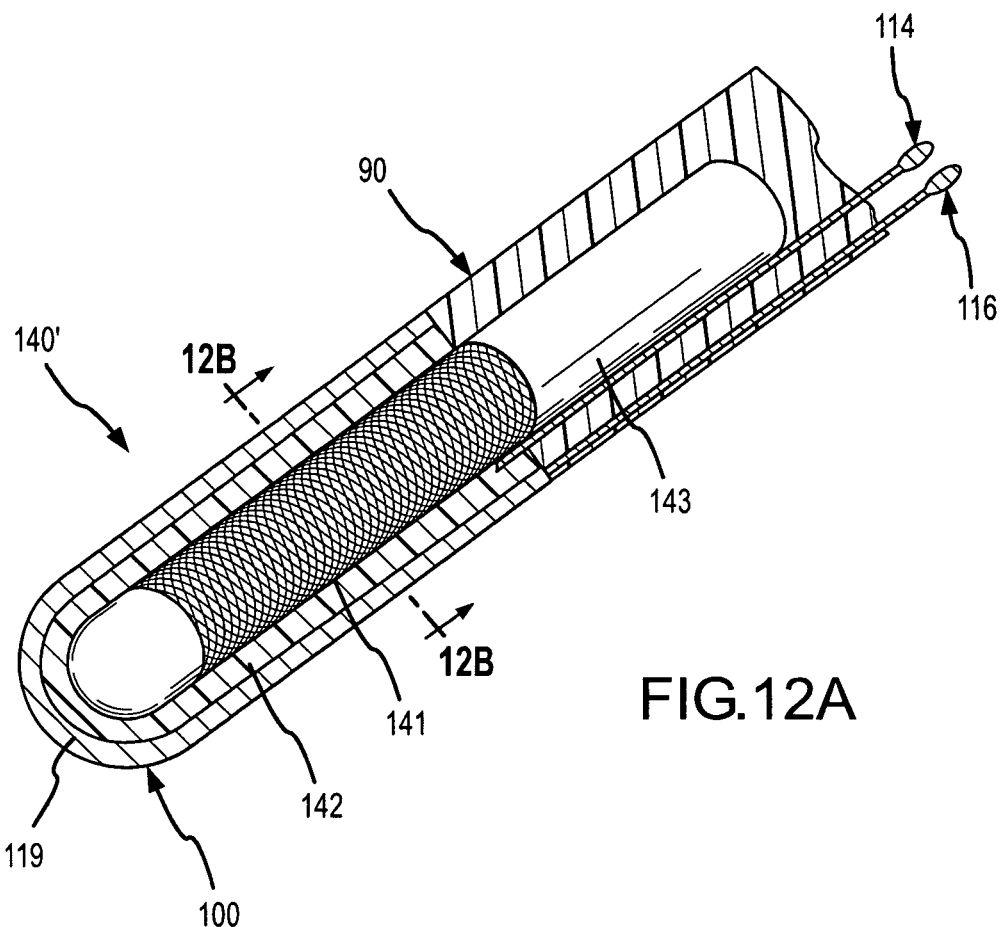
FIGS. 12A and 12B are cross-sectional views of another preferred embodiment in which the PSCC sensor is in the shape of a mesh.
Figure 12B:
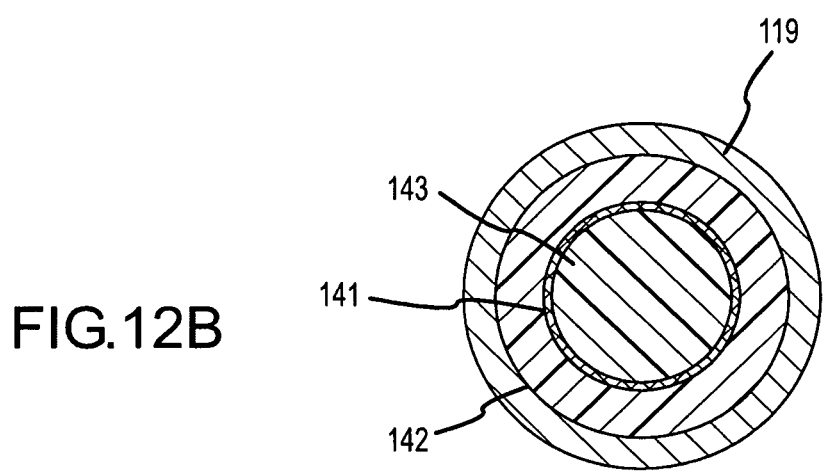

FIGS. 12A and 12B illustrate yet another preferred embodiment of the present invention, revealing two cross sectional drawings taken along the reference lines of A-A and B-B as labeled in FIG. 2. FIG. 12A is a variation of the preferred embodiment illustrated in FIG. 7A. PSCC sensor 140' extends from a catheter shaft 90, and PSCC sensor 140' comprises: flexible inner conductive sheath 141 formed of a mesh; an outer PSCC substrate layer 142; and an electrically insulative flexible shaft 143 located interiorly of the flexible inner conductive sheath 141. Flexible shaft 143 may optionally include a portion of a sphere at its distal end as shown in FIG. 7A. Flexible sheath 141 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 140' and tissue by monitoring the electrical characteristics between two nodes, namely, the conductive outer layer 119 (which is preferably measured using electrical conductor 116) and the flexible sheath 141 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 13A:
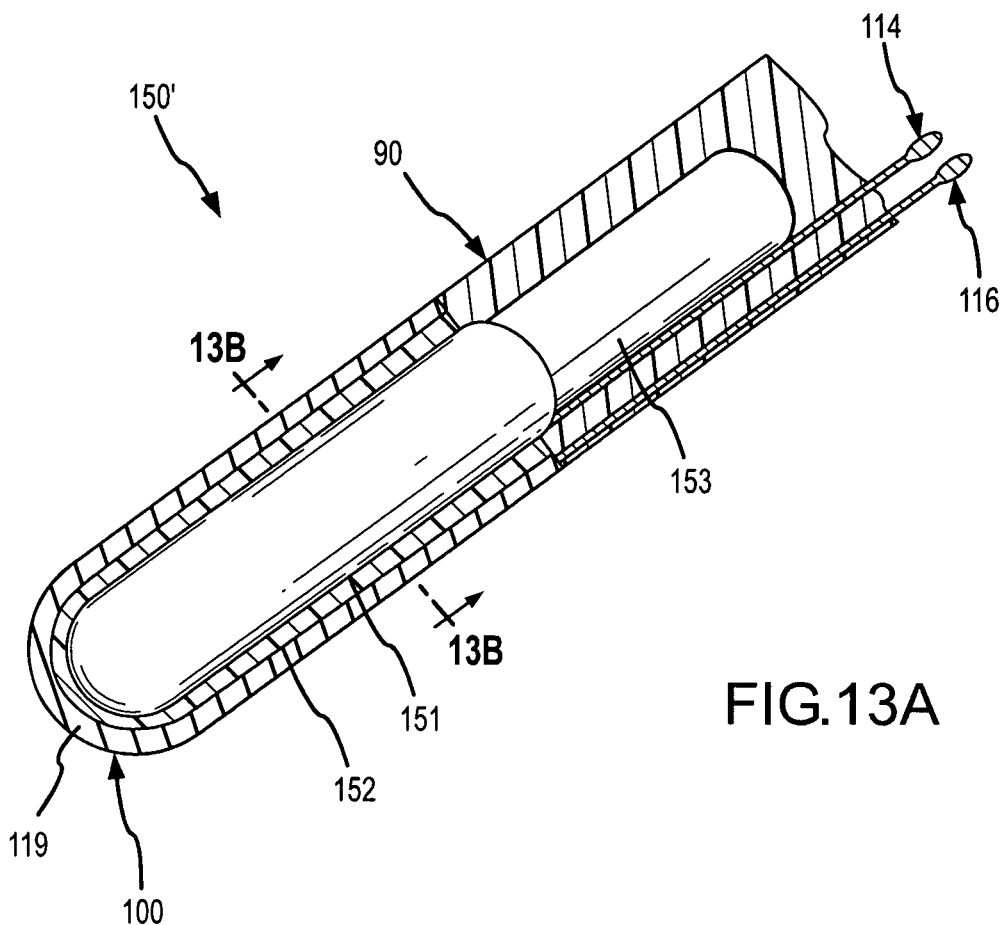
FIGS. 13A and 13B are cross-sectional views of another preferred embodiment in which the PSCC sensor is formed as an outer substrate layer.
Figure 13B:
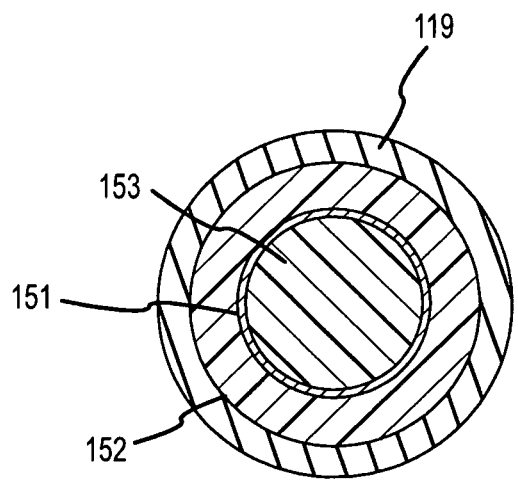

FIGS. 13A and 13B illustrates yet another preferred embodiment of the present invention, revealing two cross sectional drawings taken along the reference lines of A-A and B-B as labeled in FIG. 2. FIG. 13A is a variation of the preferred embodiment illustrated in FIG. 8A. PSCC sensor 150' extends from a catheter shaft 90, and PSCC sensor 150' comprises: an electrically insulative flexible shaft 153; a flexible inner conductive layer 151 (formed, for example, as a coating and/or wrap around flexible shaft 153); and an outer PSCC substrate layer 152. Electrically insulative flexible shaft 153 and flexible inner conductive layer 151 may optionally include a portion of a sphere at their respective distal ends (as illustrated in FIG. 13A). Flexible inner conductive core 151 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 150' and tissue by monitoring the electrical characteristics between two nodes, namely, the conductive outer layer 119 (which is preferably measured using electrical conductor 116) and the flexible inner conductive core 151 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Electrical conductors 114 and 116 may be implemented using a single conductive wire or multiple strands of wire. Preferably, the wires may be made of flexible conductive materials which allow the surface contacting area to be bent and formed into various shapes to provide better contact to the tissue. Acceptable materials include, but are not limited to, stainless steel, nickel titanium (nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

The present invention permits the construction of a flexible, pressure sensitive contact assessment device that can be used in a wide variety of different tissue environments, including for example, tissues having varying degrees of elasticity and contour.

The present invention permits the construction of a flexible sensor to measure pressure that is applied to the sensor, for example, pressure that may be applied to the sensor by the myocardium. Such sensors may be used to measure the pressure that is applied directly to the sensor, or depending on the configuration of the sensor, it may measure the pressure that is applied to a component that is in contact with the sensor (as may be the case when an additional element is disposed between a PSCC-based sensor and tissue that is exerting pressure on the additional element). In the case where a PSCC-based sensor is positioned within a catheter, the PSCC-based sensor is preferably used to measure pressure that is applied axially to catheter. Of course, the PSCC based sensor could be oriented in order to measure pressure that is applied transversely to the catheter.

While the preferred embodiments disclosed in the attached Figs. disclose a contact sensor that is generally cylindrical in shape, the present invention also contemplates that the contact sensor may be formed into various shapes to better fit the contour of the target tissue. In one embodiment, for example, the contact sensor can be made long enough to strap around and form a noose around the pulmonary veins in epicardial applications. Particularly, the conductive element that is coupled to the PSCC (for example, reference numbers 111, 121, 131, 141, and 151) may be formed into a desired shape and then the PSCC layer will be formed over the conductive element in the preferred shape. For example, the contact sensor may be shaped like a spatula for certain applications, including for example, minimally invasive sub-xyphoid epicardial applications, where the spatula shape will permit easy placement and navigation in the pericardial sac. Because PSCC can be made to be a flexible material, it can be used for form electrodes having a great variety of shapes, including a spatula.

Alternatively, the conductive element that is coupled to the PSCC may be formed using shape-memory retaining material, such as nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133, 143, and 153) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the PSCC may be formed in the shape of a helix, such as is the case with elements 121, and 131, the coil may be chosen to be of a specific stiffness (i.e., having a characteristic spring constant) that would allow the coil to exert a desired amount of pressure on the PSCC when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 5, 6 and 7, the conductive element may be mounted on an insulative shaft. The conductive element can be shaped in any number of ways, including for example, a coil, mesh, coating or wrap. The insulative shaft provides additional mechanical support in applications that require greater amounts of axial pressure and torque. The insulative shaft may be made of any electrically insulative material, including, for example, polyurethane. Preferably, the insulative shaft is made of a biocompatible, electrically insulative material.

The embodiments described above can be used with a processor such that the processor may provide more precise information about the pressures being encountered by the embodiment. In particular, any of the contact sensors described above may be used with a memory device to record information regarding one or more forces that are applied to the sensor. For example, a first known pressure may be applied to the contact sensor and a first measurement of an electrical characteristic may be made such that the first known pressure may be associated with the first measurement. Similarly, a second known pressure may be applied to the contact sensor and a second measurement of an electrical characteristic may be made such that the second known pressure may be associated with the second measurement. Additional known pressures may be applied and additional corresponding measurements may be made and associated. Then, if an unknown pressure is applied, the processor may use the known pressures and their respective associated measurements to help quantify the unknown pressure.

While the embodiments above are discussed in the context of applied pressure, the embodiments above can also be used to assess forces relative to contact between tissue and the contact sensor. Pressure is simply a measurement of the forces per unit area, and thus, to assess force, the surface area of a contact surface must be known or be capable of being determined or calculated. The force information may be derived from the information available on forces and the contact surface area.

Though not depicted, it is contemplated that each of the embodiments discussed above may optionally be used in connection with one or more electrically-conductive, outer protective coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the contact sensor's ability to assess the tissue contact (for example, in the when measuring electrical characteristics using a reference electrode connected to the target tissue). In some cases, the outer covering may be made using a biocompatible material in order to help make the overall assembly biocompatible.

Though not depicted, it is also contemplated that in certain sensor configurations, it may be desirable to optionally use an electrically non-conductive outer protective covering. In such cases, an outer covering that is electrically insulative, such as a non-conductive polymer layer (which can be porous or nonporous), may be used to increase the mechanical integrity. In some cases, the outer covering may be made using a biocompatible material in order to help make the overall assembly biocompatible. Such an electrically-non-conductive covering may also serve as a pressure transfer element to more evenly distribute pressure to the pressure sensitive conductive composite member.

One of ordinary skill will appreciate that while the PSCC materials may be designed to respond to a variety of stresses, the principles and embodiments herein may be adapted to respond to specific stress forces, for example, axial forces, orthogonal forces, twisting, compressing, stretching, etc., without deviating from the scope of the present invention.

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A sensor assembly for assessing contact between the sensor assembly and tissue, said assembly comprising:
    a catheter shaft;
    a conductive core having a first measurement terminal
    a continuous layer of a pressure sensitive conductive composite in electrical contact with said conductive core, said layer including a tissue contact surface that may be placed in contact with tissue, wherein the continuous layer of pressure sensitive conductive composite consists essentially of a non-conductive polymer substrate having a plurality of conductive particles embedded therein, and wherein the pressure sensitive conductive composite has a resistance that varies anisotropically and inversely with pressure to less than one ohm; and
    a measurement device coupled to the first measurement terminal such that said measurement device measures an electrical characteristic of the pressure sensitive conductive composite;
    wherein when the tissue contact surface applies pressure to the tissue, the measurement device will measure a change in electrical characteristics of the pressure sensitive conductive composite and provide a user with information regarding a degree of contact between the sensor assembly and the tissue being contacted.

2. The catheter assembly of claim 1 further comprising:
    a memory coupled to the measurement device for storing a plurality of electrical characteristic measurements; and
    a processor coupled to the measurement device for assessing a degree of contact using a plurality of measurements stored in the memory.

3. The catheter assembly of claim 1 further comprising:
    a conductive outer layer having a second measurement terminal, said conductive outer layer covering at least a portion of the layer of pressure sensitive conductive composite, and wherein the measurement device measures electrical characteristics of the layer of pressure sensitive conductive composite using the first measurement terminal and the second measurement terminal.

4. The catheter assembly of claim 3 further comprising:
a non-conductive outer layer covering at least a portion of the conductive outer layer.

5. The catheter assembly of claim 1 further comprising:
a reference electrode for electrically coupling to tissue, said reference electrode having a second measurement terminal;
wherein the measurement device measures electrical characteristics of the layer of pressure sensitive conductive composite using the first measurement terminal and the second measurement terminal.

6. A contact sensor assembly for assessing contact between the contact sensor assembly and tissue, said assembly comprising:
an elongate catheter body having a proximal end and a distal end;
a conductive core having a first measurement terminal, said conductive core extending at least a portion of the distal end;
a pressure sensitive conductive composite material electrically coupled to at least a portion of the conductive core located in the distal end of the catheter body, wherein the pressure sensitive conductive composite material consists essentially of a non-conductive polymer substrate having a plurality of conductive particles embedded therein, and wherein the pressure sensitive conductive composite material is an electrical insulator when in a quiescent state and has a resistance that varies anisotropically and inversely with pressure to less than one ohm;
a conductive layer having a second measurement terminal, said conductive layer covering at least a portion of the pressure sensitive conductive composite material, and said conductive layer extending at least a portion of the distal end of the catheter body;
wherein electrical characteristics of the pressure sensitive conductive composite material may be measured using the first measurement terminal and the second measurement terminal.

7. The contact sensor assembly of claim 6, further comprising:
a measurement device that measures a signal using the first and second measurement terminals and that generates an output signal that is indicative of the pressure being applied to the tissue by the distal end.

* * * * *